United States Patent
Kroll

(10) Patent No.: US 6,539,254 B1
(45) Date of Patent: Mar. 25, 2003

(54) IMPLANTABLE VENTRICULAR CARDIOVERTER/DEFIBRILLATOR EMPLOYING ATRIAL PACING FOR PREVENTING ATRIAL FIBRILLATION FROM VENTRICULAR CARDIOVERSION AND DEFIBRILLATION SHOCKS

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/153,829

(22) Filed: May 21, 2002

Related U.S. Application Data

(63) Continuation of application No. 09/452,493, filed on Dec. 1, 1999, now Pat. No. 6,442,426.

(51) Int. Cl.[7] ................................................. A61N 1/39
(52) U.S. Cl. ............................................ 607/4; 607/14
(58) Field of Search .............................. 607/4–5, 9, 11, 607/14

(56) References Cited

U.S. PATENT DOCUMENTS

| | | | |
|---|---|---|---|
| 5,007,422 A | | 4/1991 | Pless et al. .................... 28/419 |
| 5,074,301 A | * | 12/1991 | Gilli ............................... 607/4 |
| 5,203,326 A | * | 4/1993 | Collins ........................... 607/4 |
| 5,391,185 A | * | 2/1995 | Kroll .............................. 607/4 |
| 5,411,524 A | * | 5/1995 | Rahul ............................. 607/4 |
| 5,456,706 A | | 10/1995 | Pless et al. .................. 607/122 |
| 5,951,592 A | * | 9/1999 | Murphy .......................... 607/4 |
| 6,047,213 A | * | 4/2000 | Sirokman ....................... 607/9 |
| 6,169,921 B1 | * | 1/2001 | KenKnight et al. ........... 607/28 |
| 6,330,477 B1 | * | 12/2001 | Casavant ...................... 607/14 |

OTHER PUBLICATIONS

T. J. Florin, MD, et al *"Induction of Atrial Fibrillation with Low–Energy Defibrillator Shocks in Patients with Implantable Cardioverter Defibrillators,"* The American Journal of Cardiology, pp 960–962 (Oct. 1, 1997).

* cited by examiner

*Primary Examiner*—Kennedy Schaetzle
*Assistant Examiner*—Kristen Droesch

(57) ABSTRACT

An implantable ventricular cardioverter/defibrillator applies a quantity of electrical energy to a heart for terminating a ventricular arrhythmia while preventing the induction of atrial fibrillation. The cardioverter/defibrillator includes a ventricular arrhythmia detector and an atrial pacer that delivers atrial pacing pulses to an atrium of the heart when the ventricular arrhythmia detector detects a ventricular arrhythmia. A generator applies a quantity of electrical energy to the heart in timed relation to a delivered atrial pacing pulse to terminate the ventricular arrhythmia to avoid inducing atrial fibrillation.

20 Claims, 2 Drawing Sheets

IMPLANTABLE VENTRICULAR CARDIOVERTER/DEFIBRILLATOR EMPLOYING ATRIAL PACING FOR PREVENTING ATRIAL FIBRILLATION FROM VENTRICULAR CARDIOVERSION AND DEFIBRILLATION SHOCKS

CROSS-REFERENCE TO RELATED APPLICATIONS

This application is a continuation of U.S. patent application Ser. No. 09/452,493, filed Dec. 1, 1999, titled "Implantable Ventricular Cardioverter/Defibrillator Employing Atrial Pacing for Preventing Atrial Fibrillation from Ventricular Cardioversion and Defibrillation Shocks," which has now matured to U.S. Pat. No. 6,442,426 B1.

FIELD OF THE INVENTION

The present invention generally relates to an implantable ventricular cardioverter/defibrillator. The present invention more particularly relates to such a cardioverter/defibrillator which employs atrial pacing for preventing the induction of atrial fibrillation from ventricular cardioversion and defibrillation shocks.

BACKGROUND OF THE INVENTION

There is an increasing problem with ventricular defibrillation and cardioversion shocks causing atrial fibrillation. This is due to the tendency towards the use of a "single-pass" lead, the use of a "hot can" and the progressive decreasing of energy requirements for ventricular cardioversion and defibrillation. The single-pass lead, of the type known in the art, includes an atrial shock coil for positioning in the right atrium and a ventricular shock coil for positioning in the right ventricle. Hot can usage encompasses the use of the electrically conductive device enclosure as a common electrode wherein the cardioversion or defibrillation shocks are delivered from the atrial and ventricular shock coils to the electrically conductive device enclosure. Prior to the hot can approach, a subcutaneous patch electrode was used as the common electrode. With the single pass lead, the hot can approach causes more current flow through the atria than the subcutaneous patch electrode approach. The higher current though the atria can increase the probability of atrial fibrillation induction as a result of ventricular cardioversion and defibrillation Extremely high-energy shocks cardiovert or defibrillate the entire heart so as to cardiovert or defibrillate both the atria and the ventricles to thus preclude induction of atrial fibrillation during ventricular cardioversion or defibrillation. However, the modern trend is to employ more moderate energy shocks for ventricular cardioversion and defibrillation. These energy levels may not cardiovert or defibrillate the atria during ventricular cardioversion and defibrillation thus frequently the atria is in fibrillation after ventricular cardioversion or defibrillation.

The induction of atrial fibrillation by ventricular arrhythmia shock therapy causes a cascading sequence of unfortunate problems. The delivery of the ventricular shock usually occurs during a period of patient unconsciousness and is not felt. However, after atrial fibrillation is induced, the patient is left with significant anxiety that there is still an arrhythmia. This can lead to inappropriate decisions on the part of the patient, as well as the implantable ventricular cardioverter/defibrillator. For example, the implanted device can mistake the atrial fibrillation for a ventricular arrhythmia and thus cause another shock to be delivered to the patient. This second shock is often extremely painful, because the patient will now be conscious. The second delivered shock, moreover, will most likely merely serve to ensure that the patient remains in atrial fibrillation.

SUMMARY OF THE INVENTION

The invention provides an implantable ventricular cardioverter/defibrillator for applying a quantity of electrical energy to a heart for terminating a ventricular arrhythmia while preventing the induction of atrial fibrillation. The cardioverter/defibrillator includes a ventricular arrhythmia detector that detects a ventricular arrhythmia, an atrial pacer that delivers atrial pacing pulses to an atrium of the heart responsive to the ventricular arrhythmia detector detecting a ventricular arrhythmia, and a generator that applies the electrical energy to the heart in timed relation to an atrial pacing pulse delivered by the atrial pacing means. The relative timing of the generator application and the atrial pacing pulse prevents the induction of atrial fibrillation.

The implantable ventricular cardioverter-defibrillator may further include a synchronizer that synchronizes the application of the electrical energy to the heart by the generator with a delivered atrial pacing pulse.

In accordance with a further aspect of the present invention, the ventricular arrhythmia detector may include a ventricular fibrillation detector and a ventricular tachycardia detector. As a further aspect of the present invention, a ventricular antitachycardia pacer, responsive to the ventricular tachycardia detector detecting ventricular tachycardia of the heart, applies antitachycardia pacing pulses to a ventricle of the heart. An analyzer determines if the antitachycardia pacing pulses terminate the detected ventricular tachycardia. If the ventricular tachycardia is not terminated by the antitachycardia pacing, the analyzer activates the atrial pacer and generator.

In accordance with a further aspect of the present invention, the implantable ventricular cardioverter/defibrillator may include a ventricular activation detector adapted to detect ventricular activations of the heart. The atrial pacer, responsive to the ventricular activation detector, delivers the atrial pacing pulses synchronized to detected ventricular activations.

In accordance with a further aspect of the present invention, if the ventricular fibrillation detector detects ventricular fibrillation, the atrial pacer delivers the atrial pacing pulses at a substantially fixed rate. Further, the generator may include a storage capacitor and a charger that begins charging the storage capacitor to a given energy upon the detection of ventricular fibrillation and the generator applies the electrical energy to the heart from the storage capacitor when the storage capacitor is charged to the given energy.

The invention further provides a method of terminating a ventricular arrhythmia of a heart while preventing the induction of atrial fibrillation. The method includes the steps of detecting a ventricular arrhythmia, delivering atrial pacing pulses to an atrium of the heart upon detecting a ventricular arrhythmia, and applying a quantity of electrical energy to the heart in timed relation to a delivered atrial pacing pulse.

BRIEF DESCRIPTION OF THE DRAWINGS

The features of the present invention which are believed to be novel are set forth with particularity in the appended claims. The invention, together with further objects and advantages thereof may best be understood by making reference to the following description taken in conjunction with the accompanying drawings, in the several figures of which like reference characters identify identical elements, and wherein:

DETAILED DESCRIPTION OF THE PREFERRED EMBODIMENTS

Figure 1:
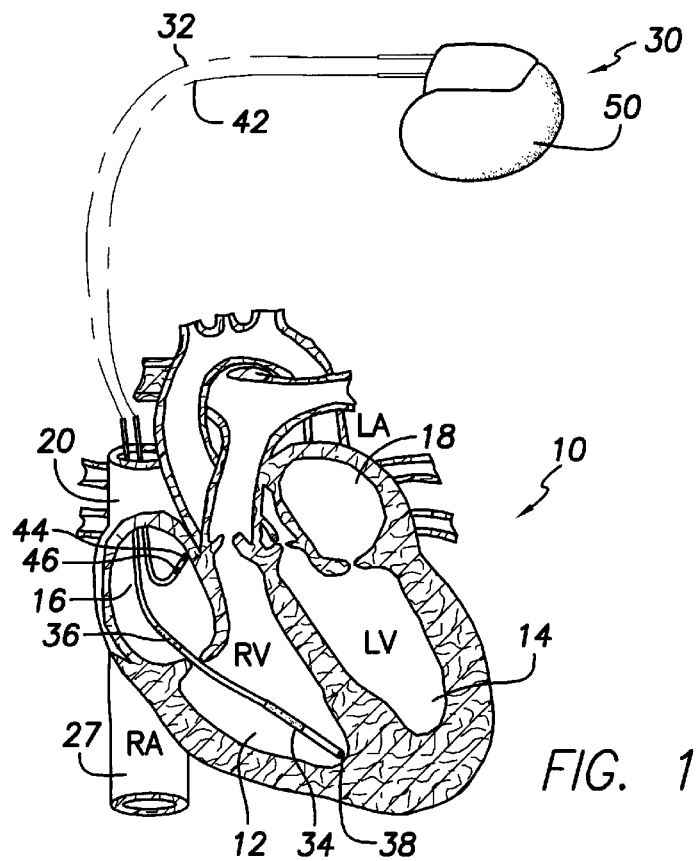
FIG. 1 is a schematic illustration of a human heart in need of ventricular arrhythmia cardioversion/defibrillation shown in association with an implantable ventricular cardioverter/defibrillator embodying the present invention.

Referring now to FIG. 1, it illustrates a heart 10 in need of ventricular arrhythmia cardioversion/defibrillation and an associated implantable ventricular cardioverter/defibrillator 30 embodying the present invention. The portions of the heart 10 illustrated in FIG. 1 are the right ventricle 12, the left ventricle 14, the right atrium 16 and the left atrium 18. Also illustrated are the superior vena cava 20 and inferior vena cava 27. As is well known in the art, the cardioverter/defibrillator 30 is arranged to be implanted in an upper left chest portion of a patient within a subcutaneous pocket.

The implantable device 30 includes a first endocardial lead 32 which is of the "single-pass" type. To that end, the lead 32 includes a first shock coil 34 arranged to be disposed within the right ventricle 12, a second shock coil 36 proximal to the shock coil 34 and arranged to be disposed within the right atrium 16 or superior vena cava 20, and a distal tip pacing electrode 38. The implantable device 30 further includes a second endocardial lead 42 having an electrode pair including a distal electrode 44 and a proximal electrode 46.

The implantable cardioverter/defibrillator 30 includes a hermetically sealed, electrically conductive enclosure 50. When a quantity of cardioverting or defibrillating electrical energy is applied to the heart 10, in accordance with this preferred embodiment, the electrodes 50 and 36 are connected in parallel and the quantity of electrical energy is applied between the parallel connected electrodes 50 and 36 and the electrode 34. Alternatively, the cardioverting and defibrillating quantity of electrical energy may be applied between electrode 34 and the electrically conductive enclosure 50 without employing electrode 36. All such cardioverting and defibrillating methodologies apply cardioverting and defibrillating electrical energy to the heart and are thus deemed to be alternative structures and methods for practicing the present invention. Electrodes 44 and 46 of lead 42 support sensing of right atrial electrical activity and, in accordance with the present invention, delivery of atrial pacing pulses to the right atrium 16.

Figure 2:
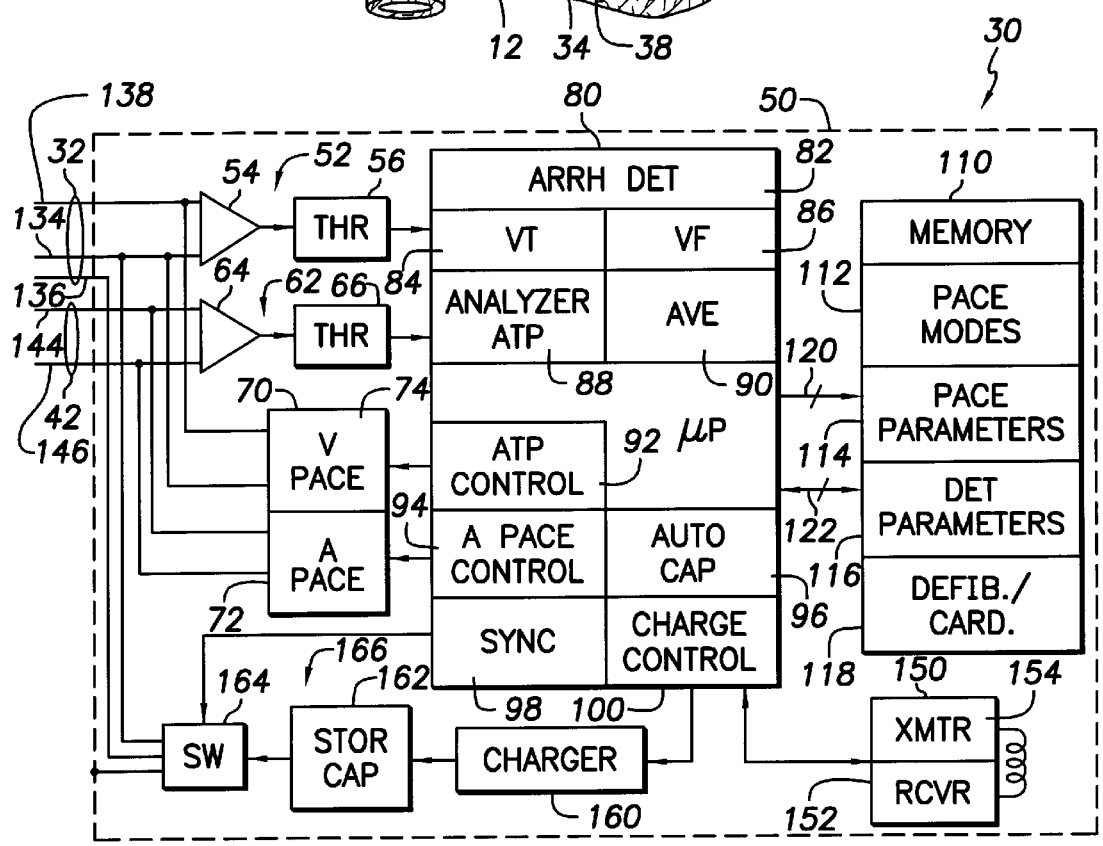
FIG. 2 is a block diagram of the implantable ventricular cardioverter/defibrillator of FIG. 1.

As illustrated in FIG. 2, the implantable cardioverter/defibrillator 30 includes within the enclosure 50 a ventricular sense channel 52, an atrial sense channel 62, and a pacing pulse generator 70 including a first or atrial pacing pulse generator 72 for providing atrial pacing pulses and a second or ventricle pacing pulse generator 74 for providing ventricle pacing pulses. The device 30 further includes a microprocessor 80, a memory 110, and a telemetry stage 150. The device 30 still further includes a cardioversion/defibrillation generator 166 including a charging circuit 160, a storage capacitor 162 and a switch 164.

The ventricular sense channel 52 includes a sense amplifier 54 and a threshold detector 56. The sense amplifier 54 has an input coupled to electrode 38 of lead 32 by a conductor 138 of the lead 32. The sense amplifier 54 has another input which is coupled to electrode 34 of lead 32 by another conductor 134 of the lead 32. The sense amplifier 54 further includes an output which forms an input to the threshold detector 56. As further illustrated, the threshold detector 56 has an output which is coupled to the microprocessor 80.

The sense amplifier 54, together with electrodes 38 and 34 sense electrical activity in the right ventricle 12. When the output from the amplifier 54 transitions through a programmed threshold of the threshold detector 56, the threshold detector 56 provides an input signal to the microprocessor 80 indicating that a ventricular activation or R-wave has been detected. Such detection is well known in the art.

Similarly, the atrial sense channel 62 includes a sense amplifier 64 and a threshold detector 66. The sense amplifier 64 has an input which is coupled to electrode 44 of lead 42 by a conductor 144 of lead 42. The sense amplifier 64 has another input which is coupled to electrode 46 of lead 42 by another conductor 146 of lead 42. As further illustrated, the sense amplifier has an output which forms an input to the threshold detector 66 and the threshold detector 66 has an output which is coupled to the microprocessor 80.

The sense amplifier 64, together with electrodes 44 and 46, sense electrical activity in the right atrium. When the output of the sense amplifier 64 transitions through a programmed threshold of the threshold detector 66, the threshold detector 66 provides an input signal to the microprocessor 80 indicating that an atrial activation or P-wave has been detected. Again, such detection is also well known in the art.

The first or atrial pulse generator 72 has outputs coupled to electrodes 44 and 46 of lead 42 by conductors 144 and 146 respectively of lead 42. This permits atrial pacing pulses produced by the atrial pacer 72 to be applied to the right atrium 16. The second or ventricular pulse generator 74 has outputs coupled to electrodes 34 and 38 of lead 32 by conductors 134 and 138 respectively of lead 32. This permits ventricular pacing pulses produced by the ventricular pacer 74 to be applied to the right ventricle 12.

The cardioversion/defibrillation generator 166 applies a quantity of cardioverting or defibrillating electrical energy to the heart 10. To that end, the charging circuit 160 charges the storage capacitor 162 with the quantity of electrical energy to be applied to the heart. The switch 164 applies the quantity of electrical energy from the storage capacitor 162 to the heart. As can be seen in FIG. 2, the switch has an output coupled to electrode 34 of lead 32 by the conductor 134 of lead 32 and another output which is coupled to electrode 36 by a conductor 136 of lead 32. Also, another output of the switch 164 is coupled to the electrically conductive enclosure 50. As a result, when cardioverting and defibrillating electrical energy is applied to the heart 10, the electrodes 50 and 36 may be coupled in parallel such that the quantity of electrical energy applied to the heart 10 is applied between the parallel coupled electrodes 50 and 36 and the electrode 34.

The microprocessor 80 controls the overall functioning of the implantable cardioverter/defibrillator 30. To implement such control, the microprocessor executes operating instructions stored in the memory 110 and utilizes various parameters also stored in memory 110. For example, the memory 110 stores the operating instructions defining the various pacing modalities which may be provided by the device 30 in a storage location 112. Pacing parameters may be stored in a storage location 114 and detection parameters for both pacing and cardioversion and defibrillation may be stored in storage location 116. Lastly, the operating instructions defining the therapy to be provided for ventricular cardioversion and defibrillation may be stored in a storage location 118.

The telemetry stage 150 permits pacing mode selections and storage of pacing, detection, and cardioversion/defibrillation parameters in the memory 110 to be made through the use of an external programmer (not shown) of the type well known in the art. The telemetry stage includes a receiver 152 which receives telemetry commands including mode selection and parameter commands from the programmer. The receiver 152 conveys the commands to the microprocessor 80 which then stores them in the memory 110. The telemetry stage 150 also includes a transmitter 154. The transmitter may be used for transmitting data to the programmer. The transmitted data may include sensed electrograms or status information, for example, as is well known in the art.

The microprocessor 80 is coupled to the memory 100 by a multiple-bit address bus 120 and a bi-directional, multiple-bit data bus 122. The microprocessor 80 uses the address bus 120 to fetch operating instructions or programmable parameters from the memory at address locations defined on the address bus 120. The fetched instructions and parameters are conveyed to the microprocessor 80 over the data bus 122. Similarly, the microprocessor 80 may store data in the memory 110 at memory locations defined on the address bus 120. The microprocessor 80 conveys the data to the memory over the data bus 122. Such microprocessor and memory operation are conventional in the art.

When executing the operating instructions stored in memory 110, the microprocessor 80 implements a number of functional stages in accordance with the present invention. Those stages include an arrhythmia detector 82 which detects the presence of a ventricular arrhythmia and which may further include a ventricular tachycardia detector 84 and a ventricular fibrillation detector 86. As will be seen hereinafter, when the arrhythmia detector 82 detects a ventricular arrhythmia, the ventricular tachycardia 84 and ventricular fibrillation detector 86 determine whether the arrhythmia is a ventricular tachycardia or a ventricular fibrillation respectively. The functional stages of microprocessor 80 further include an antitachycardia pacing analyzer stage 88, an averaging stage 90, and an antitachycardia pacing control stage 92. The functional stages of microprocessor 80 still further include an atrial pace control 94, an autocapture stage 96, a synchronizing stage 98, and a charge control stage 100.

In accordance with a primary aspect of the present invention, when the heart 10 is to receive a quantity of cardioverting or defibrillating electrical energy, the atrial pace control 94 causes the atrial pacer 72 to apply atrial pacing pulses to the atria and, more specifically, the right atrium 16. If the ventricular arrhythmia is ventricular tachycardia, the atrial pacing pulses are applied at one-half the ventricular rate and are synchronized to every other R-wave detected by the ventricular sense channel 52. If the ventricular arrhythmia is ventricular fibrillation, the atrial pacing pulses are applied by the atrial pacer 72 at a fixed rate such as, for example, 120 beats per minute. For either ventricular tachycardia or ventricular fibrillation therapy, when the required quantity of electrical energy is to be applied to heart 10, the synchronizing stage 98 operates the switch 164 for applying the cardioverting or defibrillating electrical energy to the heart synchronized to an atrial pacing pulse. In this manner, atrial fibrillation is prevented even though the cardioverting or defibrillating electrical energy is applied between the electrically conductive enclosure 50 of the device 30 (in parallel with the right atrial shock coil 36) and the right ventricular shock coil 34.

Figure 3:
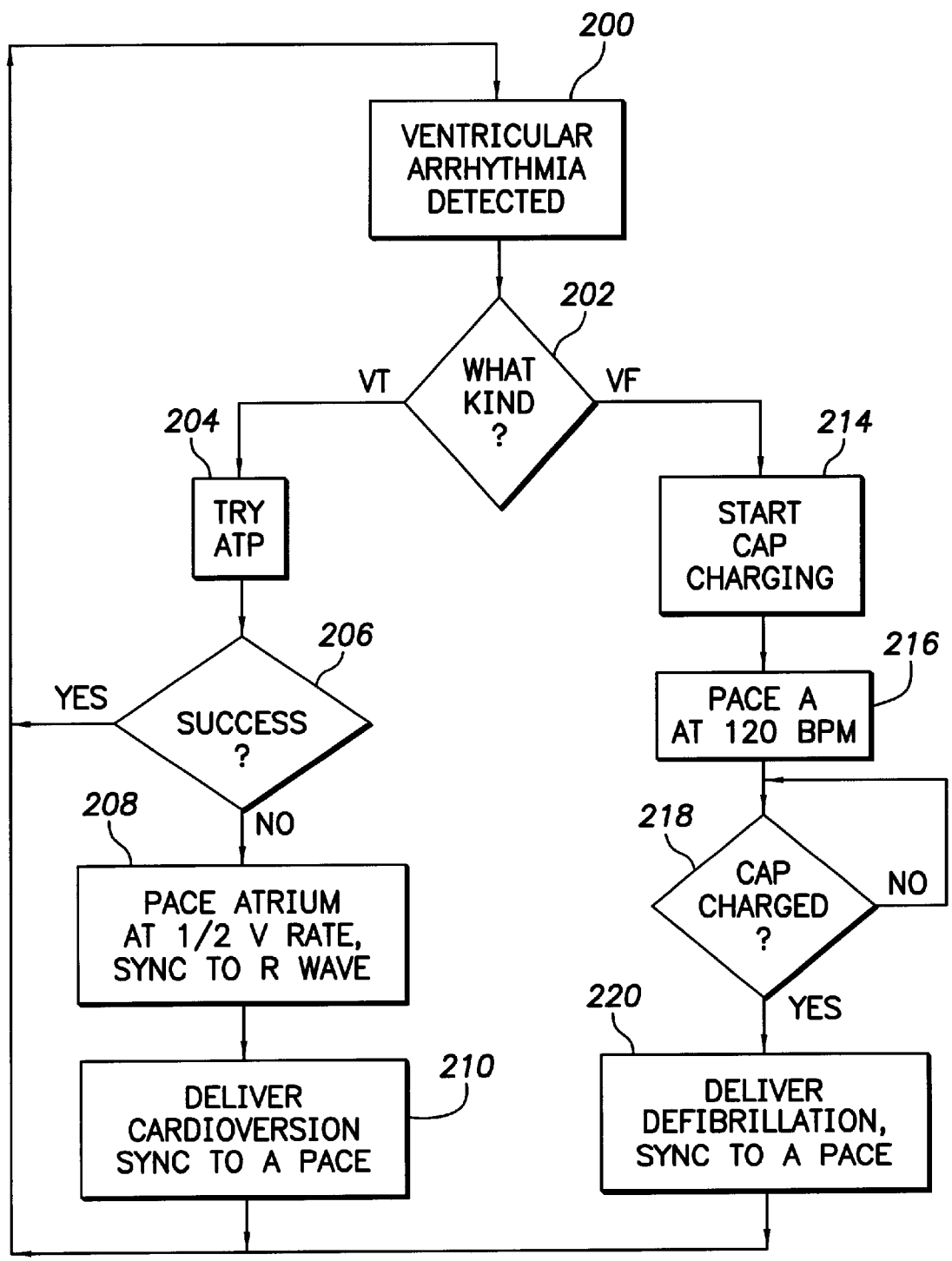
FIG. 3 is flow diagram illustrating operative steps that the device of FIGS. 1 and 2 may implement in accordance with a preferred embodiment of the present invention for providing ventricular arrhythmia therapy while preventing atrial fibrillation induction.

The foregoing and other aspects of the present invention may best be appreciated by making reference to FIG. 3 which is a flow diagram illustrating a preferred implementation of the present invention. Therapy to the heart 10 begins at step 200 when the arrhythmia detector 82 detects a ventricular arrhythmia. The arrhythmia detection criteria may be based upon ventricular rate, for example, or other criteria well known in the art.

When a ventricular arrhythmia is detected in step 200, the arrhythmia detector 82 causes a ventricular tachycardia detector 84 and ventricular fibrillation 86 to determine the nature of the ventricular arrhythmia in step 202. If the arrhythmia is ventricular tachycardia, in step 204, the antitachycardia pacing control 92 causes the ventricular pacer 74 to apply antitachycardia pacing pulses to electrodes 38 and 34 of lead 32. After a period of, for example, 10–20 seconds, the process continues to step 206 wherein the antitachycardia pacing analyzer 88 determines if the antitachycardia pacing was successful. The criteria utilized in this step 206 may include intrinsic ventricular rate. If the intrinsic ventricular rate of the heart 10 is within normal limits, the antitachycardia pacing will be considered successful and the process returns. If however it is determined that the antitachycardia pacing was not successful, the process then moves to step 208 wherein atrial pacing is initiated. In accordance with this preferred embodiment, the atrial pace control 94 causes the atrial pacer 72 to pace the right atrium 16 at one-half the ventricular rate. The pacing pulses are synchronized to every other detected R-wave. During the atrial pacing, the charge control 100 causes the charger 160 to charge the storage capacitor 162 with a predetermined quantity of energy for cardioverting the heart 10. The quantity of cardioverting energy for cardioverting the ventricular tachycardia may be, for example, on the order of five joules.

After the storage capacitor 162 is charged with the desired amount of electrical energy, the process moves to step 210 wherein the synchronizing stage 98 operates the switch 164 to cause the storage capacitor 162 to be discharged synchronized to an atrial pacing pulse. The cardioverting energy is applied using the electrically conductive enclosure 50 of the device 30 and the shock coils 34 and 36. When step 210 is completed, the process returns.

If in step 202 ventricular fibrillation is detected, the charge control 100 immediately causes the charger 160 to charge the storage capacitor 162 with an amount electrical energy required to defibrillate the heart 10. That quantity of energy may be, for example, on the order of 15 joules.

Immediately after charging of the storage capacitor is begun in step 214 and thus responsive to ventricular fibrillation being detected, the atrial pacer 72 is caused by the atrial pace control 94 to pace the right atrium in step 216. Here, the atrial pacing pulses are applied at a fixed rate and at a rate of, on the order of, 120 beats per minute. Fixed rate pacing is employed for ventricular fibrillation as discernable R-waves most likely will not be detectable.

As the atrial pacing pulses are applied by the atrial pacer 72, the process continually checks to determine if the storage capacitor 162 is charged with the desired amount of energy in step 218. Step 218 is repeated until the storage capacitor 162 is charged. When the storage capacitor is charged, which should be accomplished in a matter of a few seconds, the synchronizing stage 98 in step 220 operates the switch 164 for discharging the energy stored in storage capacitor 162 into the heart 10. The defibrillation electrical energy is synchronized to an atrial pacing pulse and is applied using the electrically conductive enclosure 50 of device 30 and the shock coils 34 and 36 of lead 32. Once the defibrillating electrical energy is applied to the heart, the process returns.

In addition to the foregoing, an additional step may be interposed in the flow diagram of FIG. 3 wherein immediately after the beginning of the atrial pacing of step 208, the autocapture stage 96 determines if the atria are being captured by the atrial pacing pulses applied by the atrial pacer 72. Such autocapture is well known in the art. If the atria are captured by the atrial pacing pulses, the atrial pacing will be permitted to continue until it is time to deliver the cardioverting energy in step 210. However, if the atrial pacing pulses are not capturing the atria, the process may immediately go to step 210 for delivering the cardioversion energy synchronized to an atrial pacing pulse.

In accordance with a further aspect of the present invention, if ventricular tachycardia is detected, the atrial pacing may be conducted in an anticipatory manner to improve the cardiac output of the heart 10. For example, if the ventricular tachycardia has a rate of 180 beats per minute, there will be a significantly reduced cardiac output. However, pacing the atrium at 90 beats per minute, just before the R-waves of the heart, could add significant cardiac output. This is due to the fact that one of the problems with ventricular tachycardia is that there is AV disynchrony, and therefore, even greater reduction of output than from the ventricular tachycardia itself. To accomplish the anticipatory pacing, the averaging stage 90 may average the time spans between a successive number of R-waves to determine the average heart rate interval. Since ventricular tachycardia is a stable arrhythmia in terms of rate, the average heart rate interval may be utilized to predict when the atrium may be paced in anticipation of the R-waves. The atrial pacing control 94 will cause the atrial pacer 72 to pace the right atrium just prior to every other R-wave. The pacing of the right atrium before every other R-wave is expected will provide improved cardiac output during the ventricular tachycardia before the heart receives a quantity of cardioverting energy using the electrically conductive enclosure 50 of the device 30 and the shock coils 34 and 36 of lead 32.

While particular embodiments of the present invention have been shown and described, modifications may be made, and it is therefore intended in the appended claims to cover all such changes and modifications which fall within the true spirit and scope of the invention.

What is claimed is:

1. An implantable stimulation device comprising:
   a ventricular arrhythmia detector;
   an atrial pacer that is operative to generate atrial pacing pulses for delivery to an atrium of the heart;
   a generator that generates one of a cardioversion and defibrillation waveform for delivery to the heart;
   a controller connected to the detector, pacer, and generator, wherein the controller is operative in response to detection of a ventricular arrhythmia by the ventricular arrhythmia detector to control the atrial pacer to generate the atrial pacing pulses, and wherein the controller is further operative to control the generator to generate the waveform in timed relation to a delivered atrial pacing pulse; and
   a synchronizer that synchronizes the application of electrical energy to the heart with a delivered atrial pacing pulse.

2. The implantable stimulation device of claim 1, further comprising a ventricular activation detector adapted to detect ventricular activations and wherein the atrial pacer, responsive to the ventricular activation detector, delivers the atrial pacing pulses synchronized to detected ventricular activations.

3. The implantable stimulation device of claim 1, further comprising an atrial activation detector adapted to detect atrial activations and a capture detector that determines if the atrial pacing pulses are capturing the atria.

4. The implantable stimulation device of claim 1, wherein the ventricular arrhythmia detector includes a ventricular fibrillation detector and a ventricular tachycardia detector.

5. The implantable stimulation device of claim 4, further comprising a ventricular antitachycardia pacer that, responsive to the ventricular tachycardia detector detecting ventricular tachycardia of the heart, applies antitachycardia pacing pulses to a ventricle.

6. The implantable stimulation device of claim 5, further comprising an analyzer that determines if the antitachycardia pacing pulses terminate the detected ventricular tachycardia.

7. The implantable stimulation device of claim 6, wherein the analyzer activates the atrial pacer and generator if the ventricular tachycardia is unterminated.

8. The implantable stimulation device of claim 4, wherein the atrial pacer, responsive to the ventricular fibrillation detector detecting ventricular fibrillation, delivers the atrial pacing pulses at a substantially fixed rate.

9. The implantable stimulation device of claim 8, wherein the generator includes a storage capacitor, wherein the cardioverter further includes a charger that begins charging the storage capacitor to a given energy upon detection of ventricular fibrillation and wherein the generator applies electrical energy from the storage capacitor when the storage capacitor is charged to the given energy.

10. The implantable stimulation device of claim 9, further comprising a synchronizer that synchronizes the application of electrical energy to the heart with a delivered atrial pacing pulse.

11. An implantable stimulation device comprising:
    a ventricular arrhythmia detector;
    an atrial pacer that is operative to generate atrial pacing pulses for delivery to an atrium of the heart;
    a generator that generates one of a cardioversion and defibrillation waveform for delivery to the heart; and
    a controller connected to the detector, pacer, and generator, wherein the controller is operative in response to detection of a ventricular arrhythmia by the ventricular arrhythmia detector to control the atrial pacer to generate the atrial pacing pulses, and wherein the controller is further operative to control the generator to generate the waveform in timed relation to a delivered atrial pacing pulse; and
    a ventricular activation detector that detects ventricular activations and wherein the atrial pacer is responsive to the ventricular activation detector for delivering the atrial pacing pulses synchronized to every other one of the detected ventricular activations.

12. The implantable stimulation device of claim 11, further comprising a synchronizer that synchronizes the application of electrical energy to the heart with a delivered atrial pacing pulse.

13. The implantable stimulation device of claim 11, further comprising:
    wherein the ventricular arrhythmia detector includes a ventricular fibrillation detector and a ventricular tachycardia detector;

a ventricular antitachycardia pacer that, responsive to the ventricular tachycardia detector detecting ventricular tachycardia of the heart, applies antitachycardia pacing pulses to a ventricle.

14. The implantable stimulation device of claim 13, further comprising an analyzer to determine if the antitachycardia pacing pulses terminate the detected ventricular tachycardia.

15. An implantable stimulation device comprising:

a ventricular arrhythmia detector;

an atrial pacer that is operative to generate atrial pacing pulses for delivery to an atrium of the heart;

a generator that generates one of a cardioversion and defibrillation waveform for delivery to the heart;

a controller connected to the detector, pacer, and generator, wherein the controller is operative in response to detection of a ventricular arrhythmia by the ventricular arrhythmia detector to control the atrial pacer to generate the atrial pacing pulses, and wherein the controller is further operative to control the generator to generate the waveform in timed relation to a delivered atrial pacing pulse; and a ventricular activation detector adapted to detect ventricular activations, a timer that times time spans between successive ventricular activations, an averager that averages a number of the time spans to predict when ventricular activations are expected, and wherein the atrial pacer delivers atrial pacing pulses prior to expected ventricular activations.

16. An implantable stimulation device comprising:

means for detecting a ventricular arrhythmia;

means for delivering atrial pacing pulses to an atrium of the heart in response to detecting a ventricular arrhythmia;

means for applying one of a cardioversion and defibrillation waveform to the heart in timed relation to a delivered atrial pacing pulse; and means for synchronizing the waveform with the delivered atrial pacing pulse.

17. The implantable stimulation device of claim 16, wherein the means for detecting comprises means for detecting ventricular fibrillation and for detecting ventricular tachycardia.

18. The implantable stimulation device of claim 17, further comprising means for applying antitachycardia pacing pulses to a ventricle of the heart in response to detecting a ventricular tachycardia.

19. The implantable stimulation device of claim 16, further comprising means for detecting atrial activations and means for determining if the atrial pacing pulses depolarize the atria.

20. A method of terminating a ventricular arrhythmia, the method comprising:

detecting a ventricular arrhythmia;

delivering one or more atrial pacing pulses to an atrium of the heart upon detecting a ventricular arrhythmia; and applying one of a cardioversion and defibrillation waveform to the heart in timed relation to a delivered atrial pacing pulse;

wherein applying comprises applying the waveform to the heart synchronized with the delivered atrial pacing pulse.

* * * * *